United States Patent [19]

Ohno

[11] Patent Number: 5,180,660
[45] Date of Patent: Jan. 19, 1993

[54] METHODS AND MATERIALS FOR HIV DETECTION

[75] Inventor: Tsuneya Ohno, Ridgewood, N.J.

[73] Assignee: Nissin Shokuhin Kabushiki Kaisha, Osaka, Japan

[21] Appl. No.: 668,745

[22] Filed: Mar. 13, 1991

Related U.S. Application Data

[60] Continuation of Ser. No. 340,710, Apr. 20, 1989, abandoned, which is a division of Ser. No. 146,371, Feb. 3, 1988, abandoned, which is a continuation-in-part of Ser. No. 64,066, Jun. 29, 1987, abandoned, which is a continuation-in-part of Ser. No. 16,282, Feb. 19, 1987, abandoned.

[51] Int. Cl.⁵ .................. C12Q 1/70; C12Q 1/00; A23J 1/00; G01N 33/53
[52] U.S. Cl. ........................... 435/5; 435/7; 530/413; 436/548; 424/7.1; 424/3
[58] Field of Search ............ 435/5, 7; 530/413; 436/548; 424/7.1, 3

[56] References Cited

U.S. PATENT DOCUMENTS

| | | | |
|---|---|---|---|
| Re. 32,833 | 1/1989 | Greene et al. | 424/86 |
| 4,490,358 | 12/1984 | Greene et al. | 424/86 |
| 4,661,445 | 4/1987 | Saxinger et al. | 435/7 |
| 4,699,880 | 10/1987 | Goldstein | 436/548 |
| 4,708,818 | 11/1987 | Montagnier et al. | 435/5 |
| 4,708,818 | 11/1987 | Montagnier et al. | 435/5 |
| 4,731,237 | 3/1988 | Reagan et al. | 424/86 |
| 4,735,896 | 4/1988 | Wang et al. | 435/5 |
| 4,784,941 | 11/1988 | Watanabe et al. | 435/5 |
| 4,816,567 | 3/1989 | Cabilly et al. | 530/387 |
| 4,908,203 | 3/1990 | Thorton | 424/86 |

FOREIGN PATENT DOCUMENTS

| | | |
|---|---|---|
| 0178978 | 4/1986 | European Pat. Off. |
| 0287226 | 10/1988 | European Pat. Off. |
| 8402848 | 8/1984 | PCT Int'l Appl. |
| 8705911 | 10/1987 | PCT Int'l Appl. |
| 8800472 | 1/1988 | PCT Int'l Appl. |
| 8801304 | 2/1988 | PCT Int'l Appl. |
| 8807375 | 10/1988 | PCT Int'l Appl. |

Primary Examiner—Christine Nucker
Assistant Examiner—Lynette F. Smith
Attorney, Agent, or Firm—Marshall, O'Toole, Gerstein, Murray & Bicknell

[57] ABSTRACT

Disclosed are immunologically active polypeptides, preferably antibodies or antibody fragments, and most preferably monoclonal antibodies, which are reactive with idiotypes of antibodies to human lymphocyte T4 protein and are reactive with the HIV virion in a manner allowing for in vitro and in vivo neutralization of HIV infectivity and detection of HIV particles in biological fluids. Presently preferred embodiments comprise monoclonal anti-monoclonal-anti-human lymphocyte T4 antibodies produced by new murine hybridoma cell lines JT4C8, JT4C12, JT4C16, JT1-1F3, JT1-1F3-E5, JT1-1D7 and JT2-N15. Also disclosed are active and passive vaccination procedures.

4 Claims, 6 Drawing Sheets

METHODS AND MATERIALS FOR HIV DETECTION

This application is a continuation of application Ser. No. 07/340,710, filed Apr. 20, 1989, now abandoned, which is a division of application Ser. No. 146,371, filed Feb. 3, 1988, now abandoned, which is a continuation-in-part of co-pending U.S. patent application Ser. No. 064,066, filed Jun. 29, 1987, which is in turn a continuation-in-part of U.S. patent application Ser. No. 016,282, filed Feb. 19, 1987.

BACKGROUND

The present invention relates generally to methods and materials useful in the diagnosis and treatment of infection with Human Immunodeficiency Virus (HIV). More particularly, the invention relates to immunologically active polypeptides, preferably antibodies or antibody fragments, and most preferably monoclonal antibodies, which are reactive with idiotypes of antibodies to human lymphocyte T4 protein and also reactive with the HIV virion in a manner allowing for in vitro and in vivo neutralization of HIV infectivity. Moreover, the invention relates to immunologically active polypeptides useful in vaccine compositions for developing protective responses to HIV infection.

The state of the art with respect to the epidemiology and immunology of the causative agent of AIDS in humans is well summarized in: Laurence, "The Immune System in AIDS", Scientific American, December, 1985, pp. 84-93; Gallo, "The First Human Retrovirus", Scientific American, December, 1986, pp. 88-98; Gallo, "The AIDS Virus", Scientific American, January, 1987, pp. 47-56; Levy et al., Science, 225, 840-842 (1984); "Mobilizing Against AIDS", Institute of Medicine, National Academy of Sciences, Harvard University Press (Cambridge, Mass 1986); and, Lane et al., Ann. Rev. Immunol., 3, pp. 477-500 (1985). The role of T4 surface glycoprotein (sometimes referred to as "CD4" protein or determinant) of human T lymphocytes in infection by HIV has been extensively studied as represented by Dalgleish et al., Nature, 312, pp. 763-767 (1984); Klatzman et al., Science, 312, 767-768 (1984); Klatzman et al., Science, 225, pp. 59-62 (1984); McDougal et al., J.Immunol., 135, pp. 3151-3162 (1985); and, Maddon et al., Cell, 47, pp. 333-348 (1986). See also, Marrack et al., "The T Cell and Its Receptor", Scientific American, February 1986, pp. 36-45; and, McDougal et al., Science, 231, 382-385 (1986).

It has recently been projected that soluble forms of CD4 may have therapeutic utility in treatment of HIV infection. See, Fisher et al., Nature, 331, 76-77 (1988); Hussey et al., Ibid, at pp. 78-81; Deen et al., Ibid, at pp. 82-83; and Traunecker et al., Ibid, at pp. 84-86 all of which relate to in vitro neutralization of HIV infectivity by soluble CD4. Among the potential drawbacks to the projected use of soluble CD4 therapeutic agents is the known reactivity of CD4 with class II major histocompatibility complex ("MHC") molecules present on the surface of other immune cells including B cells, macrophages and monocytes, leading to the suggestion that CD4 may need to be modified (e.g., by truncation) prior to attempted therapeutic use.

Numerous reports appear in the literature relating to the potential of antibodies to neutralize infectivity of HIV in vitro and in vivo and specifically to attempts at active immunization for the purpose of developing protective immunity See, e.g., Matthews et al., Proc. Nat'l. Acad. Sci. (USA), 83, pp. 9709-9713 (1986); Norman, "AIDS Therapy A New Push For Clinical Trials", Science, 230, pp. 1355-1358 (1985) and prior articles in this series; Newmark, Nature, 324, pp. 304-305 (1986); and notes appearing in Scientific American, February, 1987, at pages 86-88 under the heading, "AIDS: Hope ... And Warnings", and in New Scientist, December 18, 1986, page 7, under the heading "Can Protein T Thwart The AIDS Virus...?". See also, Mitsuya et al., Nature, 325, 773-778 (1987); Kennedy et al., Science, 231, 1556-1559 (1986); Chanh et al., EMBO Journal, 5(11), 3065-3071 (1986); Chanh et al., Eur. J. Immunol., 16, 1465-1468 (1986); Putney et al., Science, 4, 1392-1395 (1986); and, Matshushita et al., Abstract W.3.2, p.106, "III International Conference on Acquired Immunodeficiency Syndrome (AIDS), June 1-5, 1987.

Of interest to the background of the present invention are the published results of investigation into the immunological role of anti-idiotypes. See, e.g., Kennedy et al., "Anti-Idiotypes and Immunity", Scientific American, July, 1986, pp. 48-56; Jerne, "The Immune System", Scientific American, July, 1973, pp. 52-60; Marx, "Making Antibodies Without The Antigens", Science, 228, pp. 162-165 (1985); Finberg et al., CRC Critical Reviews in Immunology, 7, 269-284 (1987); and Kennedy et al., Science, 232, pp. 220-223 (1986). See, also, Norman, supra, relating to a potential correlation between anti-HIV-immunotherapy and production of anti-idiotypic antibodies to the HIV surface proteins.

Of particular interest to the background of the present invention is the work reported by McDougal et al., J. Immunology, 137, 2937-2944 (1986) wherein it was noted that: "... rabbit anti-idiotypic sera raised against each of four candidate CD4 monoclonal antibodies [OKT4A, OKT4D, OKT4F and Leu3a (sometimes referred to as "anti-Leu3a")] did not react with [HIV] virus or inhibit virus binding to CD4+T cells." This notation should be compared with the recent oral presentations of Ronald C. Kennedy at the 7th Annual DNA/Hybridoma Congress, San Francisco, March 1-4, 1987, as reported in Van Brunt, Bio-Technology, 5, 421-422 (1987), and at the III International Conference on Acquired Immunodeficiency Syndrome (AIDS), Washington D.C. June 1-5, 1987, (see, Abstract TH.9.5) as reported in New Scientist June 11, 1987 at page 26. In these presentations the development of polyclonal antisera against anti-T4 antibodies was noted, as was the capacity of such antisera to recognize HIV and partially neutralize HIV infectivity in vitro. The latter presentation also mentioned preparation of monoclonal anti-idiotype antibody and this development is also described in Chanh et al., Proc. Nat'l. Acad. Sci. (USA), 84, 3891-3895 (June, 1987).

There continues to exist a substantial need in the art for new methods and materials for diagnosis for the presence of HIV particles and HIV-infected cells in biological fluid and tissue specimens and also a substantial need for new means for effecting in vivo neutralization of the infectivity of HIV and the development of vaccination procedures conferring immunological protection against HIV infection.

BRIEF SUMMARY

The present invention provides purified and isolated immunologically active polypeptides, preferably antibodies or chimeric antibodies or fragments thereof, and most preferably monoclonal antibodies, which are reactive with idiotypes of antibodies (preferably monoclonal antibodies) to human lymphocyte T4 protein. Such products of the invention are capable of specific immunobinding with that portion of the HIV virion which is necessarily interactive with T4 surface proteins during infection by HIV of host cells such as human T lymphocytes and cells of the human nervous system. These products of the invention may be characterized, inter alia, by their strain independent capacity to neutralize infectivity of HIV in vitro, by their specific reactivity with HIV protein having a molecular weight of from about 60,000 to about 80,000 as determined by SDS-PAGE, and by their non-reactivity with class II major histocompatability molecules associated with human immune cell surfaces.

In one of its aspects, therefore, immunologically active products are generated which "respond" through specific immunobinding to HIV particles and to the surfaces of HIV-infected cells, even though they are generated without direct immunological reference to such surface proteins.

Purified and isolated polypeptides according to the invention are conspicuously suitable for use in assay procedures for the detection and/or quantification of HIV in biological fluids wherein the detection procedure is based upon immunobinding between HIV particles and reactive polypeptides (e.g., antibodies) of the invention. Moreover, antibodies, chimeric antibodies and fragments thereof developed according to the invention are selectively immunoreactive with the surfaces of HIV-infected cells and thus provide useful reagents for detection of HIV-infected cells in fluid and tissue samples and for segregation of HIV-infected cells from cell populations including both infected and non-infected cells. As such, products of the invention will be useful in diagnostic and therapeutic procedures involving separation and/or selective destruction of HIV-infected cells.

Purified and isolated immunologically active materials of the invention are also conspicuously suitable for use in anti-HIV treatment of animals, especially humans, susceptible to infection with HIV. According to one such method, immunologically effective amounts of, e.g., monoclonal antibodies of the invention, are administered to a patient either already infected with HIV or to a patient at risk of infection with HIV to develop passive immunity with respect to HIV infection. According to another method, cells infected with HIV are subjected to, e.g., in vitro segregation from non-infected patient cells and the latter may be returned to the patient.

As set forth in the following detailed description, antibody-related polypeptides of the present invention are preferably obtained by means of initial development of mono-specific antibodies (preferably monoclonal antibodies) to the human lymphocyte T4 glycoprotein (the CD4 determinant) followed by preparation of antibodies (preferably monoclonal antibodies) to the T4 idiotypic region of antibodies formed in the initial development step.

Chimeric antibodies and fragments thereof and especially bi-specific antibodies are also products within the contemplation of the present invention, as are antibody-related products produced in microbial hosts, (e.g., procaryotic and eucaryotic cells in culture) which hosts are transformed or transfected with DNA sequences encoding the desired polypeptide products.

As one example, with structural information in hand concerning the idiotypic regions of antibodies of the invention, it becomes possible to employ procaryotic and eucaryotic hosts such as E. coli, yeast, insect, and mammalian cells in culture to produce useful antibody fragments (such as fab' and f(ab')$_2$ fragments). Moreover, it is within the contemplation of the invention that chimeric antibodies (e.g. mouse/human antibodies) may be prepared using transformed mouse myeloma cells or hybridoma cells (especially heavy chain deletion mutant cells) as production hosts. Hybrid hybridoma cell producing bi-specific antibodies having diagnostic and therapeutic uses are contemplated. Recombinant methods may also be applied to the production of HIV subunit vaccine materials. For example, monoclonal antibodies of the invention are expected to be extremely well suited for the screening of expression products of HIV DNA in transformed or transfected vial or procaryotic hosts, allowing isolation of DNA encoding all or part of the amino acid sequence of naturally occurring immunologically significant HIV proteins (including glycoproteins). In suitable hosts, the presence of such DNA may allow for high level production of vaccine materials.

In a preferred form, the invention provides antibody-related polypeptides characterized as monoclonal anti-monoclonal-anti-human lymphocyte T4 antibodies. Especially preferred are monoclonal anti-OKT4 and anti-OKT4A antibodies, both of which are reactive with 60–80 Kd HIV proteins. Presently most preferred are monoclonal anti-OKT4A antibodies which have substantial capacity for in vitro neutralization of HIV infectivity of multiple HIV strains and are participative in complement-mediated cytolysis of HIV infected cells.

In another aspect, the present invention provides, for the first time, hybridoma cell lines which produce "anti-idiotypic" monoclonal antibodies specifically immunoreactive with a monoclonal antibody to human lymphocyte T4 protein in an antigen/antibody reaction. Illustratively, the present invention provides new murine-derived hybridoma cell lines, JT4C8, JT4C12 and JT4C16, JT1-1F3, JT1-1F3-E5, JT1-1D7 and JT2-N15, each of which produces, as a component of the supernatant of its growth in culture, a monoclonal antibody specifically reactive with anti-T4 idiotype and moreover reactive with HIV virion proteins in a manner expected to allow for both in vitro and in vivo neutralization of HIV infectivity.

Hybridoma cell line JT4C8 was received for deposit with the American Type Culture Collection, Rockville, Md., at the facilities of the United States Department of Agriculture, Plum Island, N.Y. on Feb. 18, 1987, with A.T.C.C. Accession No. HB9385. Hybridoma cell line JT4C12 was received for deposit with the American Type Culture Collection, Rockville, Md., at the facilities of the United States Department of Agriculture, Plum Island, N.Y. on Feb. 18, 1987, with A.T.C.C. Accession No. HB9387. Hybridoma cell line JT4C16 was received for deposit with the American Type Culture Collection, Rockville, Md., at the facilities of the United States Department of Agriculture, Plum Island, New York on Feb. 18, 1987, with A.T.C.C. Accession No. HB9386. Hybridoma cell line JT1-1F3 was received for deposit at the European Collection of Animal Cell Cultures, Salisbury, Wiltshire, U.K. on Jun. 25, 1987, with ECACC Accession No. 87062501. Hybridoma cell line JT1-1F3-E5 was received for deposit at the European Collection of Animal Cell Cultures, Salisbury, Wiltshire, U.K. on Jun. 25, 1987 with ECACC Accession No. 87062502. Hybridoma cell line JT1-1D7 was received for deposit by the Fermentation Research Institute, Ibaragi-ken, Japan on Jan. 29, 1988 with the Accession No. FERM BP-1685. Hybridoma cell line JT2-N15 was received for deposit by the Fermentation Research Institute, Ibaragi-ken, Japan on Jan. 29, 1988 with the Accession No. FERM BP-1684.

In still another of its aspects, the present invention provides for production of HIV subunit vaccine materials by means of well-known affinity purification methodologies whereby HIV protein fractions (especially those in the molecular weight range of from about 60,000 to about 80,000 and most especially about 65,000-67,000) are isolated through use of a selective immunoabsorbants prepared using antibodies of the invention.

Numerous aspects and advantages of the present invention will be apparent upon consideration of the illustrative examples and descriptions of practice of the invention in the following detailed description thereof and the drawing, wherein: FIGS. 1, 2 and 3 graphiclly represent the results of immunoreactivity testing of antibodies of the invention with HIV and non-infected cell proteins; FIGS. 4 and 5 provide immunoblot assay results involving antibodies of the invention and HIV proteins; and FIGS. 6A through 6E provide photographic results of immunofluorescent staining assays on infected and uninfected cells employing antibodies of the invention.

DETAILED DESCRIPTION

Figure 1:
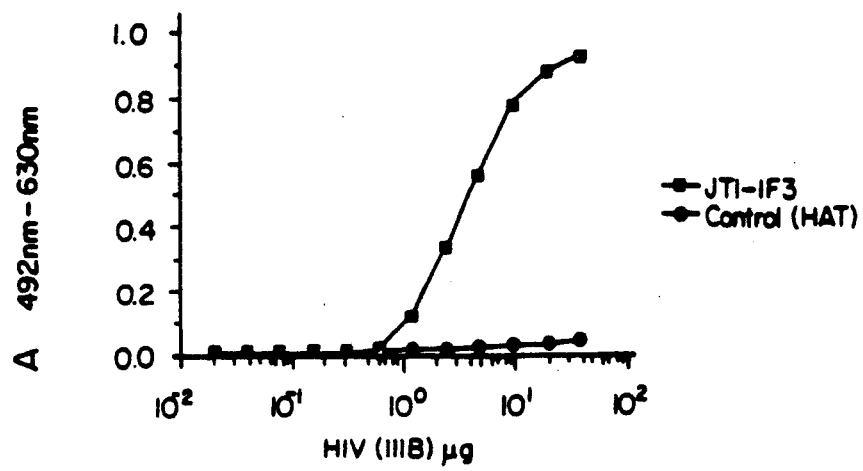

The following examples illustrate practice of the invention in the production of a number of hybridoma cell lines including JT4C8, JT4C12, JT4C16, JT1-1F3, JT1-1F3-E5, JT1-1D7 and JT2-N15 the isolation therefrom of monoclonal antibodies to anti-CD4, and the amplification and characterization of such monoclonal antibodies.

More particularly, Example 1 is directed to stimulation of a murine host toward production of antibodies to a commercially available anti-T4 monoclonal antibody, "OKT4", the fusion of spleen cells with myeloma cells, the screening, cloning and growth of hybridoma cells, and the isolation of monoclonal antibodies therefrom. Example 2 relates to the characterization of monoclonal antibodies so produced by fluorescent immunoassay, by Western blot assay for reactivity with HIV protein, and by screening for capacity to effect in vitro neutralizaitn of HIV infectivity. Example 3 relates to a first procedure for development of hybridoma cell lines capable of providing in the medium of their growth monoclonal antibodies to the commercially available antibody "OKT4A". Example 4 relates to characterization of monoclonal antibodies so produced by means of immunofluorescence assay, Western blot assay, in vitro neutralization assay, ELISA assay, and fluorescent cell staining assays. Example 5 relates to a second procedure for development of hybridoma cell lines capable of providing in the medium of their growth monoclonal antibodies to the commercially available antibody "OKT4A" and to characterization of monoclonal antibodies so produced by means of Western blot assay, and in vitro neutralization assay.

EXAMPLE 1

According to one aspect of the practice of the invention, hybrid tumor cell lines are produced using standard immunological techniques such as described in Oi and Herzenberg, Selected Methods Cell Immunology, 351-372 (1979) and Godding, "Antibody Production By Hybridomas", J.Immunol.Meth., 39, pp. 285-308 (1980). Spleen cells from mice, hyperimmunized with monoclonal anti-T4 are fused with a mouse myeloma cell line in the presence of polyethylene glycol. The supernatant from growth of each "hybridoma" cell culture is tested for the presence of the desired antibody activity. Selected hybridoma cells are cloned to propagate cell lines which produce an antibody in their growth culture supernatant, which antibody has highly specific anti-anti-T4 activity.

A. Immunization

BALB/C mice each were subject to splenic injection with monoclonal anti-human lymphocyte T4 antibody (OKT4, Ortho Diagnostics, Rahway, N.J.).

One miligram of the lyophilized OKT4 material was brought up in 1 ml of distilled water. Dialysis was employed to remove and replace the original phosphate buffer with 50 mM MES buffer (Sigma Chemicals), pH 6.0. The material was then subjected to high pressure liquid chromatography separation on FPLC® apparatus (Pharmacia, Laboratory Separation Division, Piscataway, N.J. 08854). Separation was carried out using a Mono Q column under recommended procedures except that the salt gradient was changed to 0 to 0.5M NaCl. Aliquots (20 $\mu$l) of each 0.5 ml fraction were assayed for activity using freshly collected human lymphocytes ($10^5$ cells per ml). More specifically, cells and HPLC fractions were mixed and centrifuged. The cells were then washed several times and resuspended in phosphate buffered saline (PBS). 5 $\mu$g rabbit anti-mouse IgG labelled with FITC was incubated with the cells. Following centrifugation, the cell pellet was resuspended in PBS and results were read using a fluorometric cell counter. Fractions displaying highest activity were pooled, analyzed on SDS-PAGE and were revealed to be greater than 90% pure.

Each of 4 mice was initially given a splenic injection totalling approximately 100 $\mu$l of inoculant (approximately 1.5 $\mu$g OKT4 per mouse). Fourteen and twenty-eight days later the mice were each given booster injections of 100 $\mu$l inoculant.

Four days after the final booster, the mice were sacrificed and spleens were removed aseptically and placed in petri dishes (on ice) containing Dulbecco's Modified Eagle's Medium (Gibco). The spleens were trimmed of fat and connective tissue, passed through 100 gauge stainless steel mesh. The resulting individual spleen cells were pelleted by centrifugation for 10 minutes at 1000 rpm. The cell pellet was washed twice with media (as above) and was resuspended in RPMI 1640 and the cell concentration was determined by counting in a hemocytometer in the presence of 0.2% trypan blue.

Mouse myeloma cells NSl/1.Ag4.1 derived from Balb/c strain, were grown in RPMI 1640 medium containing 15% heat-inactivated horse serum (Pel-Freeze). The cells were pelleted by centrifugation at 1000 rpm for 10 minutes and washed with RPMI 1640 containing no antibiotic. The cell concentration was determined by counting after resuspension in the same medium.

Spleen and NSl/1 cells were combined in a ratio of 4:1 and centrifuged at 1000 rpm for 10 minutes. The supernatant fluid was aspirated away and cell fusion was conducted at 37° C using polyethylene glycol (PEG) 1500, molecular weight 500-600. The procedure was carried out with constant gentle stirring by addition of the following, at the times indicated: 1.0 ml of 50% PEG in RPMI 1640 added over one minute, with one minute stirring, 1.0 ml RPMI 1640 containing 15% horse serum over one minute; 1.0 ml of RPMI 1640 containing 15% horse serum added over one minute; and 8 µl RPMI 1640 containing 15% horse serum added over 2 minutes.

The resulting fused cells were centrifuged at 1000 rpm for 10 minutes, resuspended in RPMI 1640 containing 15% horse serum and also containing penicillin G and streptomycin at 100 units and 100 mg per ml, respectively. The cells were plated at 0.1 ml per well in 96-well plates previously equilibrated in 5% $CO_2$.

Plates were incubated overnight at 37° C. in 5% $CO_2$. On day two, each well received 0.1 ml of HAT medium (13.6 µg/ml hypoxanthine 0.176 µg/ml aminopterin and 3.88 µg/ml thymidine) in RPMI 1640 containing 15% horse serum. This medium selectively allows spleen cell NS1/1 hybrids to survive, screening out unfused NS1/1 cells or those fused to other cells. Unfused primary spleen cells from adult mice will not survive in culture for more than a few days.

On days 3, 4, 6, 9 and 12, 0.1 ml of medium was removed from each well, and 0.1 ml of fresh HAT in RPMI 1640 containing 15% horse serum was added. On days 15, 19, 23 and 27, 0.1 ml of medium was removed from each well, and was replaced with 0.1 ml of RPMI 1640 containing 15% horse serum and only hypoxanthine and thymidine in the same concentration as above. On day 28, culture supernatants from all wells were screened for detection of antibody specific for OKT4.

A fluorescent-linked immunosorbent assay ("FLISA") was utilized for the detection of hybridomas producing antibodies to OKT4. Wells of 96-well plates were coated overnight at 37° C. with 100 µl of carbonate bicarbonate solution containing 3.0 µg/ml of rabbit anti-mouse IgGFc. Wells were washed ten times with PBS containing 0.05% Tween 20. The wells were blocked for 1 hour at 37° C. with 20% horse sera. Blocking agent was removed by two washings with PBS/Tween 20 as above.

Twenty microliter aliquots of culture fluid from each hybridoma well and 80 µl PBS were incubated in the coated wells at room temperature for 1 hour and then at 4° C. overnight. The wells were washed ten times with PBS containing 0.05% Tween 20 and blocked with 150 µl/well mouse serum (8 µg/ml), incubated for 3 hours at 37° C. and then 2 hours at 4° C.

100 µl of FITC-labelled OKT4 (0.3 µg/ml) was incubated in each well overnight and in the dark at 4° C. Wells were washed 10 times with PBS/Tween 20 solution as above. To each well was added 200 µl of $5 \times 10^{-5}$ N NaOH and $5.6 \times 10^{-4}$N $NH_4OH$ solution. The plates were maintained at room temperature for 15 minutes and then shaken for 1 minute. After transfer to Titertek Microtitration 1×8 plates, the wells were fluorometrically (excitation 490 nm; emission 530 nm) using a Corona Electric model MTP 100F microplate reader.

Of the 2710 wells screened, 19 were significantly positive for reaction with OKT4. The 19 positive clones were designated JT4Cl through JT4C19.

Formal cloning of hybridoma cells obtained from the positive wells was conducted by diluting the cells into additional wells at a ratio such that there was approximately 1 cell per 3 wells. Generally, formal cloning from an active well produced formal clones which appeared to be subclones of the same hybridoma cell but in several instances revealed different clone populations over three generations. Subclones from the same original well were named with the parent number and an additional number (e.g., clones obtained from well JT4C7 were labeled JT4C7-1, JT4C7-2, etc.).

EXAMPLE 2

In order to characterize the antibodies produced by the positive clones described in Example 1, tests were conducted to determine relative affinity of monoclonal antibodies the original immunogen, the antibodies were also screened by Western blot analysis for immunoreactivity with HIV virion proteins, and the antibodies were screened for capacity to neutralize infectivity of HIV virus.

A Relative Affinity Titrations

A fluorescent-linked assay was carried out according to the same general procedure employed for antibody screening in Example 1, except that various dilutions of rabbit anti-mouse IgG Fc were deposited in test wells. Fluorescence results are set out in Table 1 for antibodies derived from clones JT4Cl through JT4C-13 and JT4C16. Fluorescence results for various subclones of JT4C7 are set out in Table 2.

The data in Table 1 indicate that antibodies of clones JT4Cl, JT4C2 and JT4C4 are of relatively high affinity. Antibodies from clones JT4Cll and JT4C13 are of relatively lower affinity, with the antibodies of the remaining clones tested being of an intermediate affinity.

Correspondingly, Table 2 reveals that of the subclones of JT4C7, clones JT4C7-12 and JT4C7-9 are respectively of the highest and lowest relative affinity in this test procedure.

TABLE 1

| Concentration Anti-Mouse Antibody (µg/ml) | Clone No. | | | | | | | | | | | | | | |
|---|---|---|---|---|---|---|---|---|---|---|---|---|---|---|---|
| | 0 (Blank) | 1 | 2 | 3 | 4 | 5 | 6 | 7 | 8 | 9 | 10 | 11 | 12 | 13 | 16 |
| 10 | −27 | 2882 | 2799 | 2511 | 2913 | 2529 | 2435 | 2601 | 2395 | 2523 | 2463 | 1003 | 2281 | 1151 | 2203 |
| 3 | 271 | 877 | 803 | 823 | 938 | 723 | 688 | 763 | 617 | 751 | 716 | 405 | 830 | 497 | 620 |
| 1 | 37 | 201 | 200 | 236 | 128 | 178 | 133 | 199 | 84 | 98 | 112 | 92 | 215 | 192 | 272 |
| 0.3 | 24 | 31 | 17 | 106 | 37 | 99 | 109 | 142 | 38 | 88 | 76 | 101 | 397 | 185 | 263 |
| 0.1 | 205 | 14 | −1 | 123 | 23 | 49 | 53 | 103 | 19 | 49 | 61 | 16 | 117 | 70 | 157 |
| 0.03 | 392 | 21 | −82 | 76 | 68 | 66 | 55 | 120 | 43 | 43 | 125 | 76 | 104 | 107 | 202 |
| 0.01 | 301 | 15 | 23 | 105 | 54 | 88 | 46 | 85 | −51 | 40 | 103 | 31 | 80 | 60 | 198 |
| 0.003 | 17 | −8 | −43 | 86 | −14 | 116 | 42 | 115 | −27 | 29 | 126 | 26 | 51 | 65 | 136 |

TABLE 2

| Subclone No. | Concentration Anti-Mouse Antibody (μg/ml) | | | | | | | | | | |
|---|---|---|---|---|---|---|---|---|---|---|---|
| | 3.0 | 1.5 | 0.75 | 0.37 | 0.18 | 0.09 | 0.045 | 0.022 | 0.011 | 0.005 | 0.002 |
| JT4C7-3 | 2364 | 1004 | 399 | 337 | 267 | 259 | 217 | 206 | 246 | 215 | 161 |
| JT4C7-12 | 2480 | 914 | 376 | 298 | 278 | 262 | 232 | 200 | 249 | 230 | 202 |
| JT4C7-8 | 2420 | 869 | 351 | 291 | 236 | 214 | 235 | 201 | 217 | 188 | 208 |
| JT4C7-9 | 2238 | 924 | 366 | 270 | 289 | 214 | 250 | 211 | 214 | 245 | 251 |
| JT4C7-6 | 2441 | 864 | 344 | 250 | 234 | 210 | 243 | 210 | 203 | 239 | 235 |
| JT4C7-4 | 2372 | 869 | 369 | 275 | 249 | 243 | 233 | 204 | 228 | 227 | 229 |
| JT4C7-11 | 2330 | 828 | 378 | 290 | 268 | 246 | 224 | 211 | 245 | 228 | 227 |
| HAT Medium | 786 | 475 | 248 | 306 | 241 | 237 | 245 | 200 | 220 | 242 | 272 |

B Western Blot Analysis

Antibodies derived from all nineteen positive clones identified in Example 1 were assayed by Western blot analysis for immunoreactivity with proteins of the HIV virion. More specifically, HTLV-IIIB particles were disrupted with SDS (0.1%) and dithiothriotol (0.003M) and the material was placed on a 7.5% polyacrylamide gel, the gel was electrophoresed using standard procedures and materials were transferred to nitrocellulose filter paper. Filters were initially incubated with 20% heat inactivated horse serum in PBS for 1 hour and then washed with PBS. Filters were then incubated with antibody supernatants of each clone for 3 hours at room temperature with gentle shaking and then overnight at 4° C. with gentle shaking. After washing with PBS/Tween 20, and re-blocking with 20% horse serum as above for one hour, 10 μg of peroxidase labelled rabbit anti-mouse IgG was added and the mixture was incubated at room temperature for 4 hours. After 10 washings with PBS/Tween 20, color was developed by standard means. Antibodies derived from clones JT4C8, JT4C12 and JT4C16 all strongly reacted with HIV protein having a molecular weight of about 60,000 to 80,000. The ability of these antibodies to immunoreact with HIV protein that played no part in their generation is strongly predictive of the capacity of these antibodies to effect neutralization of HIV in vitro and in vivo.

Isotype analysis of the above-noted antibodies reactive in Western blot procedures revealed that JT4C12 and JT4C16 antibodies were of the $IgG_3$ isotype.

C. HIV Neutralization

Hybridoma culture supernatants were tested for HIV neutralization capacity in the following manner. Three day growth supernatants were diluted 1:5 in complete medium [500 ml RPMI 1640; 6 ml 100×Penicillin/-Streptomycin; 6 ml 100×L-glutamine; 100 ml FCS; and, 1.2 ml Polybrene Stock (1 mg/ml)]. 200 μl of the medium-diluted sample was added to all but two wells of a 24 well microtiter plate and two wells received an equal quantity of medium alone. Additional medium was added to one of the "medium-only" wells and each remaining well received 200 μl of high titer HIV virus stock. Plates were sealed in plastic bags, incubated for 1-1½ hours at 4° C. and allowed to return to 17° C. upon standing for about 15 minutes. H9 cells were incubated in complete medium for 30 minutes at 37° C. at a density of $1 \times 10^6$ cells/ml, then centrifuged and resuspended in fresh complete medium at a density of $5 \times 10^6$ cell/ml. 200 μl of the cell suspension was added to each well (bringing the total volume to 600 μl) and the plates were incubated for 1 hour at 37° C., whereupon 150 μl was transferred to a duplicate plate containing 2.0 ml of fresh complete medium per well. Cultures were incubated at 37° C. in a $CO_2$ incubator. After 4 days, the cultures were split and fresh complete medium was added. At day 7 of incubation samples were prepared for neutralization screening by IFA and Reverse Transcriptase procedures. [See, Guroff et al., Nature, 316, 72–74 (1985); Matthews et al., Proc. Nat'l. Acad. Sci. (USA), 83, 9709–9713 (1986); and Poiesz et al., Proc. Nat'l. Acad. Sci. (USA), 77, 7415–7419 (1980)]. In a first neutralization screening procedure, the results were essentially negative or inconclusive but in a second procedure commenced concurrently with the running of the first, antibodies from 12 of 15 tested clones in the JT4Cl-19 series displayed neutralizing activity in the IFA or RT test or both and 5 of 6 antibodies of the JT4C7 subclones tested displayed neutralization characteristics. All neutralization was "partial" in comparison to human AIDS (HTLV-IIIB) patient serum which displayed 100 percent neutralization in these assays.

EXAMPLE 3

The general hybridoma forming and screening procedures of Example 1 were repeated using the commercially available monoclonal anti-human lymphocyte T4 antibody designated OKT4A (Ortho Diagnostics, Rahway, N.J.) which was purified using a Mono S (rather than Mono Q) column. The specific immunization procedure varied slightly from that of Example 1 in that the initial injection was intraperitoneal and involved approximately 15 μg of purified antibody. The second intraperitoneal inoculation was seven days later and consisted of approximately 10 μg of purified antibody. Thirteen days later, the final booster of about 5 μg of antibody was administered by splenic injection. Of 2090 wells screened, 34 were significantly positive for reaction with OKT4A, with 10 of these displaying high activity (fluorescence values of about 1000 or more against a "background" of approximately 200). These ten positive clones were designated JT1-1D11, JT1-1F3, JT1-1G2, JT1-6E12, JT1-6F12, JT2-8E9, JT3-2C4, JT3-5A11, JT3-6D9, AND JT3-6E8.

EXAMPLE 4

In order to characterize the antibodies produced by the positive clones described in Example 3, tests were conducted essentially as described in Example 2. Briefly, supernatant antibodies were reactive on the Western blot assay with HIV protein having a molecular weight of from about 60,000 to about 80,000. The assays predominantly indicated reaction with an approximately 67,000 molecular weight protein, with some antibodies showing reactivity with a 78,000 molecular weight species. Significantly no reactivity was noted with 41 Kd or 120 Kd fractions usually characterized as the major immunologically significant HIV envelope glycoproteins. Of the antibodies displaying the strongest reaction, two (JT1-6E12 and JT2-8E9) were of an IgM isotype and the antibody of clone JT1-1F3 was of the IgG1 isotype. Set out below in Table 3 are the results of the fluorescent-linked assay for employing the JT1-1F3 antibody.

TABLE 3

| Concentration Anti-Mouse Antibody (μg/ml) | Blank | Control (HAT) | JT1-1F3 |
|---|---|---|---|
| 20 μg/ml | 4 | 754 | 1093 |
| 10 | −37 | 738 | 1010 |
| 5 | −43 | 756 | 899 |
| 2.5 | −56 | 759 | 908 |
| 1.25 | −2 | 454 | 634 |
| 0.625 | −38 | 291 | 325 |
| 0.313 | 23 | 315 | 310 |
| 0.157 | 11 | 340 | 331 |

Neutralization studies carried out concurrently with those of Example 2(C) also indicated initial negative neutralization results and, in the second trial, only slight evidence of neutralization capacity on the RT assay. Nonetheless, the IgG1-secreting JT1-1F3 clone was selected for ascites amplification and further antibody ELISA screening for reactivity with HIV protein.

In the first ELISA screen, varying concentrations of HTLV-IIIB protein (respectively, concentrations of 40, 20, 10, 5, 2.5, 1.25, 0.625, 0.313, 0.156, 0.078, 0.039 and 0.020 μg/ml) were coated onto microtiter plates, blocked (20% horse serum/PBS, 37° C., 2 hours), and dried overnight. Culture supernatant (20 μl with 80 μl PBS) or HAT medium control was added as a first antibody. After one hour of incubation at room temperature and storage at 4° C. overnight, peroxidase conjugated rabbit anti-mouse IgG (0.3 μg/ml in 5% horse serum/PBS) was added as the second antibody. After 2 hours of incubation at room temperature, substrate was added (O-phenylenediamine, 0.5 mg/ml in McIlvan's Buffer, pH 5.5; 10 Ml of 3% hydrogen peroxide). After 20 min. of incubation at room temperature, t reaction was stopped with 50 μl 0.4M sulfuric and absorbance was read at λ492–610. The test are graphically represented in FIG. 1 that HIV was detectable at levels of 1.25 μg and also that reactivity progressively increased with up to 40 μg of virus.

Figure 2:
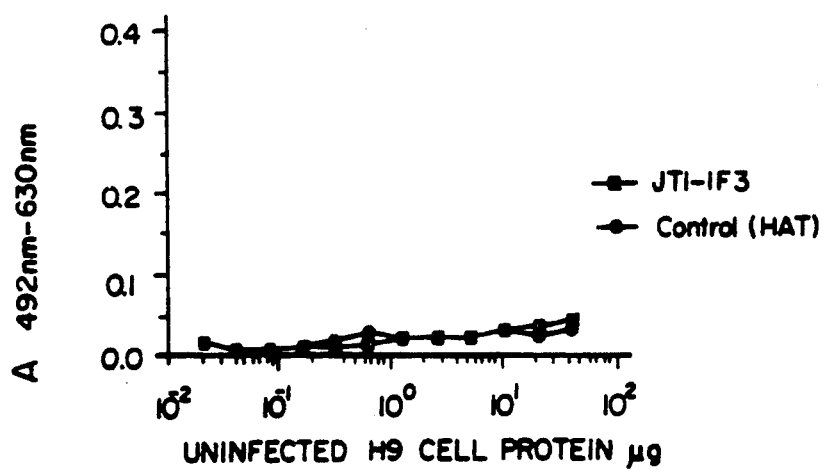

The ELISA procedure was repeated on plates initially coated with varying concentrations of uninfected H9 cell membrane preparation [$10^6$, $6 \times 10^5$, $4 \times 10^5$, $2 \times 10^5$, $6 \times 10^4$, $4 \times 10^4$, $2 \times 10^4$, $1 \times 10^4$, $6 \times 20$ $10^3$, $4 \times 10^3$, $2 \times 10^3$ cells/ml]. The results of this test procedure are graphically represented in FIG. 2 and indicate no reactivity with non-infected preparations.

Figure 3:
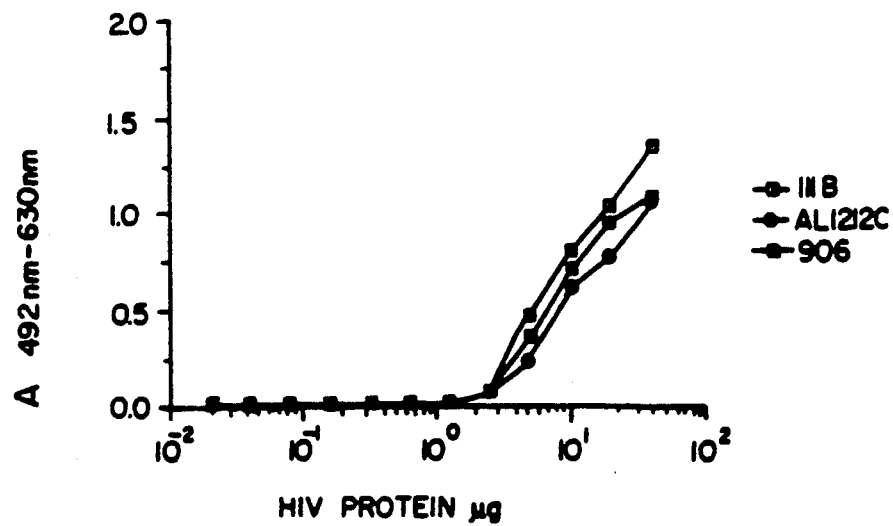

Finally, the HIV protein ELISA was repeated using the same varying concentrations of protein from the HTLV-IIIB HIV variant, the Haitian HIV variant designated AL1212C (obtained from Dr. David Hall, Massachusetts General Hospital, Boston, Mass.) and the African HIV variant designated 906 (obtained form Dr. Jerome Groopman, New England Deaconess Hospital, Boston, Mass.). As graphically illustrated in FIG. 3, the JT1-1F3 antibody recognized a common epitope of all three HIV variants.

Ascites fluid derived JT1-1F3 antibody was then tested for in vitro neutralization activity as indicated by the RT assay described above and by syncitium induction. In this procedure a comparison was made between varying levels of JT1-1F3 antibody (ascites fluid IgG fraction), a negative control (ascites fluid/pristane) and a positive control in the form of serum from an HTLV-IIIB-infected patient. According to this procedure, HIV strains IIIB, AL1212C and 906 were incubated with Mab JR1-lF3, control ascites or neutralizing human serum (in a 1:5 dilution in phosphate buffered saline) for 90 minutes at 4° C. H9 cells ($5 \times 10^6$) were then added to each well and incubated for 1 hour at 37° C. Aliquots (150 μl) were removed from each well and added to 2.0 ml fresh medium. The cultures were split 1:1 on day 4. Reverse transcriptase activity and syncytium induction were monitored on day 4 and day 7. The day 7 results of this procedure are provided in Table 4, wherein the relative syncytium induction is indicated as follows: (−), 0/200 cells; (+/−), 1–5/ 200 cells; (+), >10% cells; (++), >25% of cells; and (+++), >50% of cells.

TABLE 4

| | JT1-1F3 NEUTRALIZATION | | | | | |
|---|---|---|---|---|---|---|
| | HIV = HTLV-III B | | HIV = AL1212C | | HIV = 906 | |
| | RT Activity/ % Neutralization | Syncitium Induction | RT Activity/ % Neutralization | Syncitium Induction | RT Activity/ % Neutralization | Syncitium Induction |
| 1. Non-infected H9 | 5100/— | — | 3420/— | — | 4800/— | — |
| 2. HIV | 135150/0 | +++ | 317280/0 | +++ | 627510/0 | +++ |
| 3. HIV + 1 mg/ml Ab | 5730/100 | — | 12030/96.2 | — | 56970/90.9 | — |
| 4. HIV + 600 μg/ml Ab | 50700/62.4 | — | 130380/58.9 | +/− | 431670/31.2 | — |
| 5. HIV + 300 μg/ml Ab | 78330/42.0 | ++ | 240030/24.3 | + | 497850/20.6 | +/− |
| 6. HIV + 50 μg/ml Ab | 132780/1.7 | +++ | 198690/37.4 | +++ | 647670/0 | ++ |
| 7. HIV + Ascites (control) | 168000/0 | +++ | 281100/11.4 | +++ | 765000/0 | +++ |
| 8. HIV + Human Serum | 5460/100 | — | 197130/37.8 | ++ | 688680/0 | +++ |

The results shown in Table 4 clearly demonstrate in vitro neutralizing activity for the JT1-1F3 antibody versus all three HIV variants tested, in contrast to the neutralizing activity for infected patient serum, which was completely variant-specific, indicating recognition by the monoclonal antibody of a significant type-common epitope.

Figure 4:
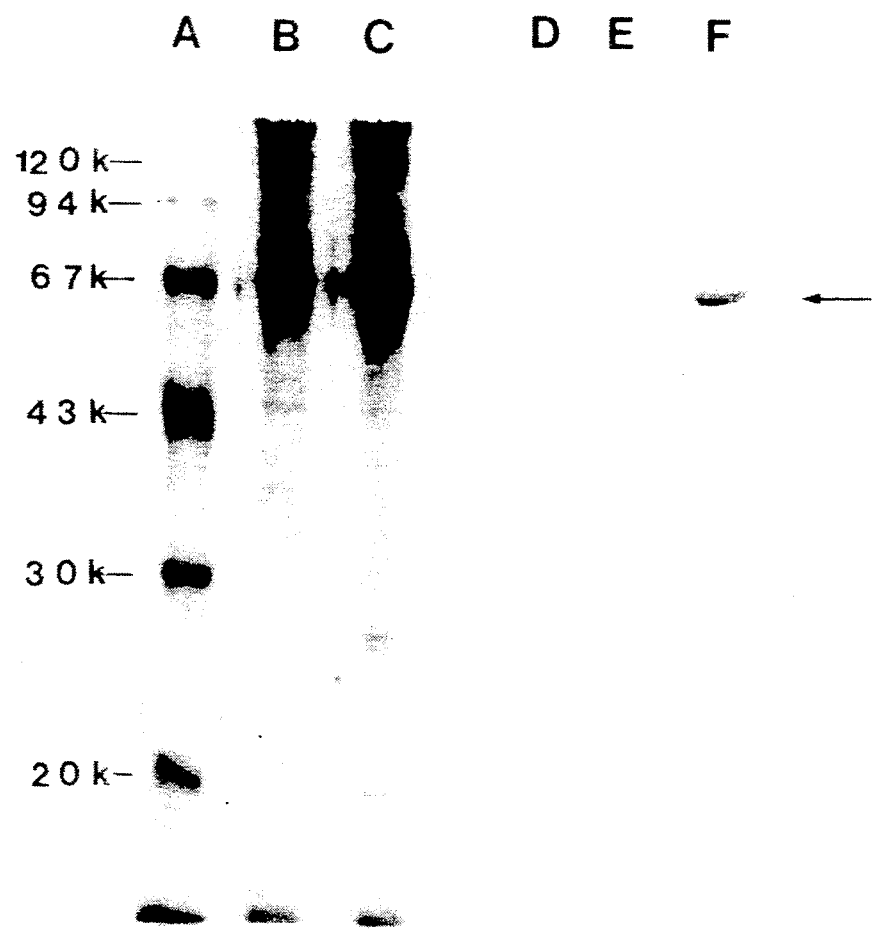

The molecular weight of the JT1-1F3 antibody reactive species was determined by immunoblotting. Purified HTLV-IIIB (5 and 10 μg) was analyzed by SDS-PAGE and Coomasie blue/silver staining (FIG. 4, Lanes B and C). Similar aliquots were analyzed by SDS-PAGE, transferred to nitrocellulose paper and analyzed for reactivity with JT1-1F3 antibody. A single reactive species was detectable at approximately 67 kd (FIG. 4, Lanes E and F).

Figure 5:
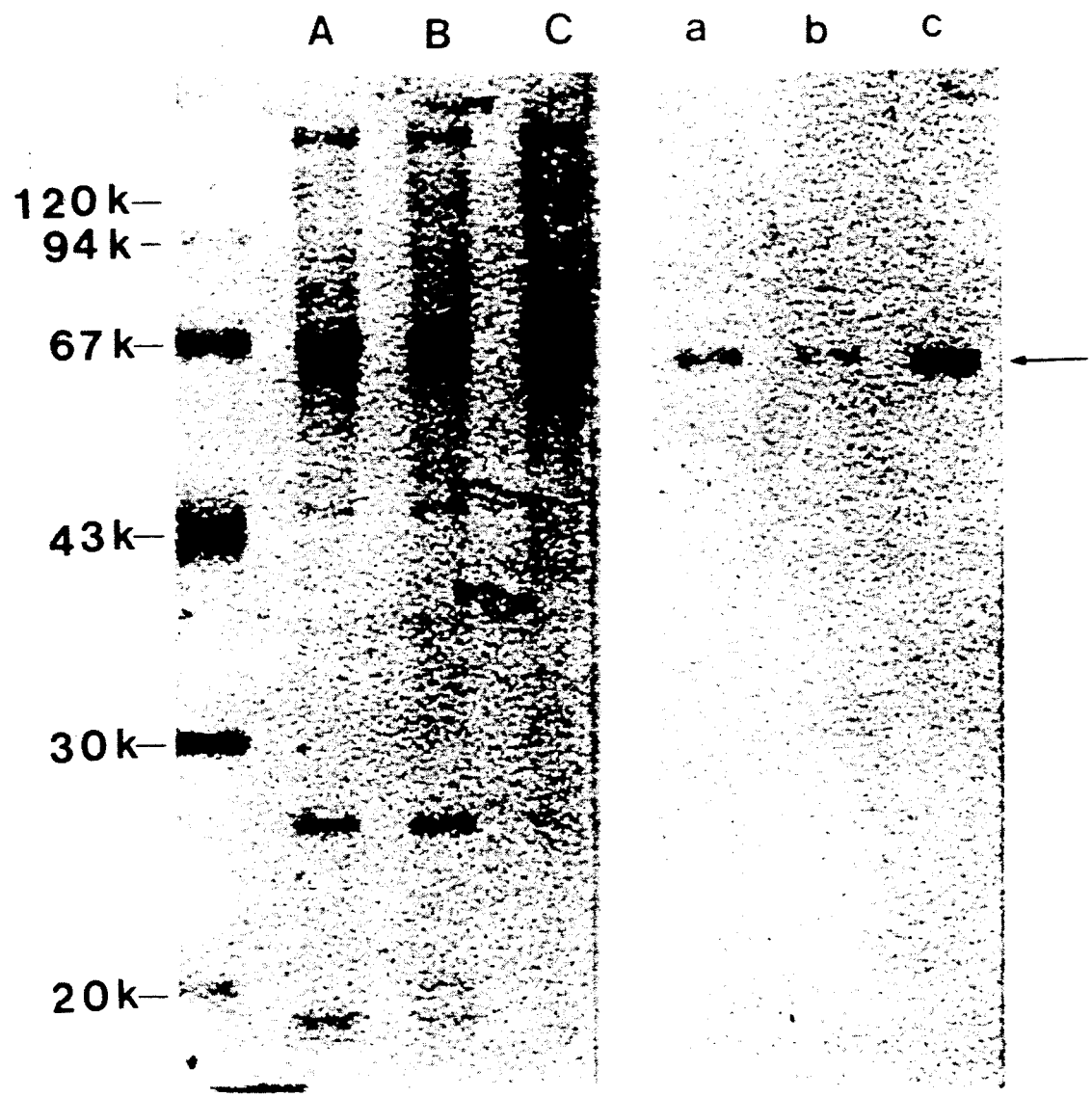

Reactivity of JT1-1F3 antibody with the HTLV-IIIB isolate was compared to that with other HIV stains. Similar patterns of reactivity by ELISA were obtained with the HTLV-IIIB, AL1212C and 906 strains. Furthermore, Western blot analysis with JT1-1F3 antibody and each of the three HIV strains revealed reactivity with antigens of similar molecular weight (FIG. 5). These findings indicate that MAb JT1-1F3 reacts with related or identical antigens detectable in divergent HIV strains.

Figure 6A:
Figure 6B:
Figure 6C:
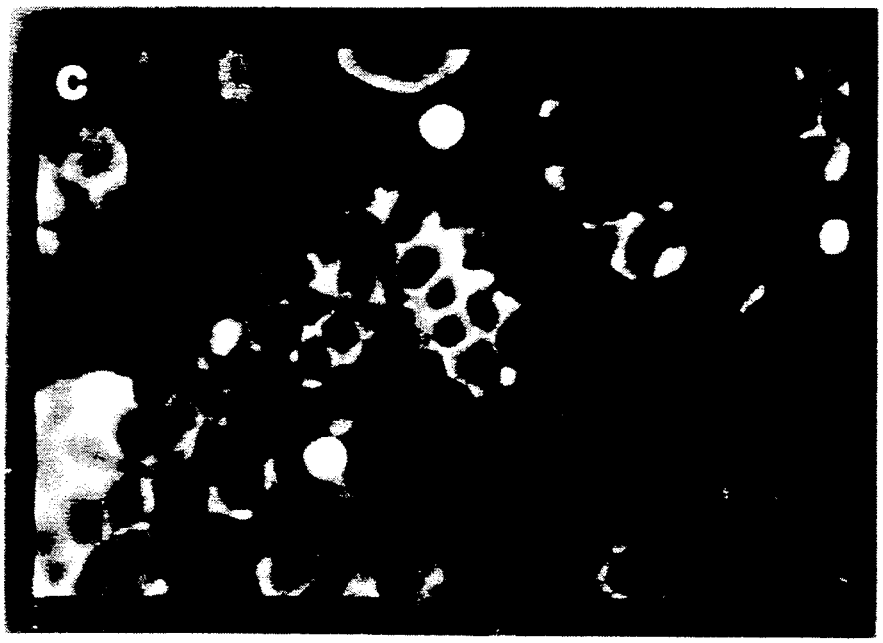
Figure 6D:
Figure 6E:

The above findings with JT1-1F3 antibody suggested that it might also be useful in detecting HIV virus-infected cells. In this regard, the binding of JT1-1F3 antibody (ascites fluid IgG fraction) to uninfected and HIV-infected H9 cells was monitored. The extent of JT1-1F3 finding was determined by a fluoresceinated rabbit anti-mouse IgG. As shown in FIG. 6A, there was little if any detectable binding of antibody to uninfected H9 cells. In contrast, focal and diffuse binding of the antibody was detectable with HTLV-IIIB-infected H9 cells (FIG. 6B). Similar findings were obtained when using H9 cells infected with the 906 and AL1212C strains (FIGS. 6C and D). This approach has been extended to hematopoietic cells from a patient with AIDS. Mononuclear cells were collected from peripheral blood of the AIDS patient by Ficoll-Hypaque separation and examined for reactivity with JT1-1F3. As shown in FIG. 6E, a focal and diffuse immunofluorescent staining pattern was detected with these cells that was similar to the findings obtained with HIV-infected H9 cells.

It is noteworthy that screening of the JT1-1F3 antibody for reactivity with cells possessing class II major histocompatibility ("MHC") surface components (i.e., human B cell line MD1 and normal peripheral blood mononuclear cells) reveal no substantial reactivity.

Subcloning of the JT1-1F3 resulted in the selection of subclones JT1-1F3-E5 and JT1-1D7 as respectively producing progressively higher levels of IgG$_1$ antibody than JT1-1F3. Comparative neutraliziation assay data for JT1-1F3, JT1-1F3-E5 and JT1-1D7 is set out in Table 5 below. Reactivity within the ELISA assay format for the antibodies produced by these three hybridomas is set out in Table 6 below.

EXAMPLE 5

The hybridoma forming and screening procedures of Examples 1 and 3 were again repeated using OKT4A, with the following variations in the immunization procedure. The initial immunization involved intraperitoneal injection of 10 μg of Mono S purified OKT4A antibody; the second intraperitoneal injection (7 μg) was given seventeen days later; and the final, 7 μg intravenous dose was administered 18 days later. After fusion and screening, an IgG$_1$-producing positive clone, designated JT2-N15 was selected for further study. Like JT1-1F3 and its subclones JT1-1F3-E5 and JT1-1D7, clone JT2-N15 produced a monoclonal antibody which was reactive on the Western blot assay with HIV protein having a molecular weight of about 65–67,000. Culture media from growth of JT2-N15 was positive in the ELISA assay and the results in a preliminary neutralization assay with respect to HIV-IIIB infectivity are set out in Table 7 below.

TABLE 7

| Neutralization of HIV-IIIB By JT2-N15 | |
|---|---|
| | RT Activity and % Neutralization |
| 1. Non-infected H9 | 157/— |
| 2. HIV | 12194/0 |
| 3. HIV + 1.5 mg/ml Ab | 343/98.5 |
| 4. HIV + 750 μg/ml Ab | 568/96.6 |

TABLE 5

| | HIV = HTLV-III B RT Activity/ % Neutralization | HIV = AL1212C RT Activity/ % Neutralization | HIV = 906 RT Activity/ % Neutralization |
|---|---|---|---|
| JT1-1F3 | | | |
| 1. Non-infected H9 | 464/— | 455/0 | 494/0 |
| 2. HIV | 10976/0 | 58131/0 | 127317/0 |
| 3. HIV + 4 mg/ml Ab | 5823/49.0 | 15754/73.5 | 27212/78.9 |
| 4. HIV + 2 mg/ml Ab | 8561/23.0 | 47571/18.3 | 156653/0 |
| 5. HIV + 400 μg/ml Ab | 7183/36.1 | 515261/11.5 | 1803291/0 |
| JT1-1F3-E5 | | | |
| 1. Non-infected H9 | 126/0 | 121/— | 126/— |
| 2. HIV | 10990/0 | 33501/0 | 16213/0 |
| 3. HIV + 2.9 mg/ml Ab | NT* | 9281/72.6 | NT |
| 4. HIV + 1.9 mg/ml Ab | NT | 11559/65.7 | — |
| 5. HIV + 1 mg/ml Ab | 552/96.1 | 17967/46.5 | 2253/86.8 |
| 6. HIV + 500 μg/ml Ab | 775/94.0 | NT | 3894/76.6 |
| JT1-1D7 | | | |
| 1. Non-infected H9 | 214/0 | | |
| 2. HIV | 10998/0 | | |
| 3. HIV + 500 μg/ml Ab | 177/100 | | |
| 4. HIV + 250 μg/ml Ab | 1549/87.6 | | |

*NT = Not Tested

TABLE 6

| Comparison of 3 Hybridoma on ELISA | | | | |
|---|---|---|---|---|
| HIV-IIB Viral Protein | JT1-1F3 | JT1-1E5 | JT1-1D7 | Control (Culture Media) |
| 10 | 1.337 | 1.111 | 1.392 | 0.031 |
| 5 | 0.914 | 0.887 | 1.118 | 0.023 |
| 2.5 | 0.996 | 0.831 | 1.081 | 0.022 |
| 1.25 | 0.499 | 0.278 | 0.523 | 0.011 |
| 0.63 | 0.221 | 0.122 | 0.176 | 0.020 |
| 0.31 | 0.070 | 0.075 | 0.060 | 0.015 |
| 0.16 | 0.048 | 0.049 | 0.036 | 0.004 |
| 0.08 | 0.027 | 0.027 | 0.031 | 0.012 |

In further screening procedures for neutralizing activity of anti-idiotype antibodies propagated by the ascites method, it has been preliminarily determined that the following protocol generates the most active ascites preparation. Five to eight week old mice are "primed" with 0.5 to 1.0 ml Pristane and two weeks later injected with 2 to 8 × 10$^6$ (preferably about 5 × 10$^6$)

hybridoma cells. Collection of ascites fluids commenced two weeks after inoculation and the initial fluids collected (about 3-5 ml) displayed the highest neutralization activity. A second collection of ascites fluid carried out three days later produced from 8 to 10 ml of fluid having lesser activity. A third collection from surviving animals generally provided 3-5 ml of fluid which, at times, was substantially less active than either of the materials from the first and second collection. Neutralization data shown for JT1-1F3 in Tables 4 and 5 was based on ascites pooled from three collections whereas data for JT1-1F3-E5, JT1-1D7 and JT2-N15 in Tables 5 and 7 was based on ascites materials pooled from first and second collections only.

While the foregoing illustrative examples have been directed to procedures involving the commercially available monoclonal antibody preparations OKT4 and OKT4A, other commercial antibodies such as Leu3a (Becton-Dickenson, Immunocytometry Systems, Mountain View, Calif., 94039) are expected to be equally suitable for use in generating anti-idiotype antibodies according to the invention. Equally suitable are non-commercial antibodies (preferably monoclonal antibodies) prepared by known hybridoma techniques using human T cells, human T lymphoblast cells which express the T4 glycoprotein and recombinant-produced human T4 protein isolates as the initial immunogen. Moreover, while antibodies produced by JT1-1F3 and its subclones and JT2-N15 are of the IgG1 isotype, it is expected that antibodies of differing isotypes will be equally useful. Antibodies of the $IgG_2$ isotype, for example, may be more useful in procedures involving complementmediated cytolytic reactions.

Confirmation of the operability of the procedures of the present invention is provided by the reports of Chanh et al., *P.N.A.S. (USA)*, 84, 3891-3895 (June, 1987) wherein it is reported that monoclonal antibody to Leu3a (designated HF1.7) was capable of in vitro neutraliziation of HIV-IIIB infectivity. However, neutralizing activity of HF1.7 has been characterized as "weak"[see Weiss, Nature, 331, p. 15 (January, 1988)] and has not been demonstrated to extend to strains other than HIV-IIIB. Moreover, unlike the anti-OKT4 and OKT4A mononoclonal antibodies of the foregoing examples, the anti-Leu3a antibody of Chanh et al. is not indicated as reactive with any HIV-derived protein other than gp120 as shown in FIG. 4 at page 3894 of Chanh et al., supra. [See also, Dalgleish et al., The Lancet, ii, 1047-1050, November 7, 1987, relating to polyclonal anti-Leu3a antibodies.]

While the foregoing examples relate to murine-derived hybridoma cell preparations, it is within the contemplation of the invention to generate and employ hybrid hybridomas (e.g., mouse/human) and especially human/human hybridomas prepared, for example, in a manner consistent with Borrebaeck, *TIBTECH*, June, 1986, pp. 147-153; Abrams et al., *Methods in Enzymology*, 121, pp. 107-119 (1986); Kozbor et al., *Methods in Enzymology*, 121, pp. 120-140 (1986); Suresh et al., *Methods in Enzymology*, 121, pp. 210-228 (1986); and Masuho et al., *Biochem. & Biophys. Res. Comm.*, 135(2), pp. 495-500 (1986). See, also, Klausner, "'Single Chain' Antibodies Become a Reality", *Bio/Technology*, 4, 1042-1045 (1986), Klausner, "Stage Set For 'Immunological Star Wars'", *Bio/Technology*, 5, 867-868 (1987) and Marx, "Antibodies Made To Order", *Science*, 229, 455-456 (1985).

It will be readily understood, therefore, that the above specific illustrative methodologies for the production of hybridomas and the identification and isolation of monoclonal antibodies are not intended to be restrictive of the scope of practice of the invention. Numerous alternative methodologies exist for achieving the same results as demonstrated, for example, by articles appearing in *Methods in Enzymology, Vol.* 121, "Immunochemical Techniques, Part I", Langone et al., eds., Academic Press, Inc. (New York, 1986).

It is also within the contemplation of the invention to develop immunologically active polypeptides for use in diagnostic and therapeutic methods of the invention by means of expression of DNA sequences encoding therefor in suitably transformed or transfected procaryotic and eucaryotic host cells in culture.

Anti-HIV therapeutic methods of the invention will be understood to comprise the administration of effective amounts of antibodies or antibody fragments of the invention to a patient infected with HIV or at risk of HIV infection in order to generate passive immunity involving neutralizing infectivity of HIV in vivo. In this regard, combination of products of the invention with immunologically acceptable diluents, adjuvants and carriers is contemplated in order to form immunologically effective anti-HIV therapeutic compositions.

Anti-HIV therapeutic methods of the invention within the contemplation of the invention also comprehend active immunization using biologically active HIV protein fractions reactive with the monoclonal antimonoclonal anti-human lymphocytes. Such products may be obtained directly from virus preparations by well known affinity purification processes involving forming immunological reaction mixtures between HIV proteins and antibodies of the invention, followed by isolation of the desired protein. As one example, the 60,000 to 80,000 molecular weight HIV protein recognized by the JT1-1F3 in procedures of Example 4 is a prime candidate for vaccine use. The same is expected to be true for recombinant expression products based on HIV DNA which can be immunologically identified (and/or purified) by means of antibodies of the invention.

Diagnostic methods of the invention wherein polypeptide products are employed to detect and quantify HIV particles in biological fluids such as blood are expected to form an essential part in preliminary screening for patients who would benefit from passive immunization according to the invention and in the monitoring therapeutic regimens of the invention.

The finding that antibodies of the invention are selectively reactive with the surfaces of HIV-infected cells is indicative of a variety of diagnostic and therapeutic utilities including histological screening of tissue (e.g., lymphatic cells) and fluid (e.g., blood) samples for detection of HIV infection, possibly at early stages of infection not readily detectable by assays based on screening for antibodies. Recognition of infected cells by antibodies of the invention allows for segregation of such cells from cell populations comprising both infected and non-infected cells. It is thus contemplated that blood of AIDS patients may be subjected to extracorporeal treatment to remove or selectively kill infected lymphocytes through use of antibodies of the invention. Moreover, within the contemplation of the invention is in vivo treatment with antibodies of the invention coupled with supplementation of circulating complement to effect cytolysis of infected cells. Support for the operability of such a therapeutic protocol is provided by preliminary positive results of tests for the capacity of JT1-1D7 antibodies to participate in the in vitro complement dependent cytolysis of HIV infected H9 cells.

Selective reactivity properties of antibodies make them good candidates for in vivo drug or toxin delivery to infected cells and use in development of bi-specific antibodies which will include double determinants allowing for, e.g., "focusing" effector T cell activity. See, e.g., Staerz et al., *Proc. Nat'l. Acad. Sci. (USA)*, 83, 1453-1457 (1986).

Based on the fact that the present invention has its foundation in the immunological characteristics of T4 protein—which is believed to provide the common receptor for HIV infection by all variants (e.g., AL1212C, 906, ARC, LAV, HTLV-IIIRF, HTLV-IIIB)—rather than any specific HIV variant, it is expected that diagnostic and therapeutic methods of the invention will be applicable to detection and treatment of infection involving all HIV variants. Use of polypeptides of the invention as diagnostic and research tools is expected to provide additional information into the nature of the interaction between HIV and host cells. As one example, monoclonal antibodies of the invention will be useful in identifying the precise primary, secondary and tertiary structural conformation of region(s) of surface proteins of HIV and host cells which are specifically and necessarily interactive in the recognition and association processes involved in HIV infection of cells. This information, in turn, would allow for generation of immunologically active materials of the invention through use of synthetic and recombinant-produced peptide immunogens.

The foregoing detailed description has been given for clearness of understanding only and no unnecessary limitations should be understood therefrom inasmuch as numerous modifications and variations will be expected to occur to those skilled in the art.

What is claimed is:

1. A method for segregating HIV-infected cells in a population of infected and non-infected cells, said method comprising forming an immunological reaction mixture of said cell population and a purified and isolated immunologically active polypeptide in the form of an antibody or chimeric antibody or antibody fragment capable of specific immunobinding with that portion of the HIV virion which is necessarily interactive with T4 surface proteins during HIV infection of host cells and characterized by the capacity to neutralize infectivity of HIV in vitro and by specific immunoreactivity with an antibody immunospecific for human lymphocyte T4 and segregating infected from non-infected cells on the basis of the selective binding of said polypeptide to infected cells.

2. A method for segregating HIV-infected cells in a population of infected and non-infected cells, said method comprising forming an immunological reaction mixture of said cell population and a monoclonal anti-monoclonal-anti-human lymphocyte T4 antibody and segregating infected from non-infected cells on the basis of the selective binding of said antibody to infected cells.

3. A method for isolating HIV proteins from a fluid sample, said method comprising contacting said sample with a purified and isolated immunologically active polypeptide in the form of an antibody or chimeric antibody or antibody fragment capable of specific immunobinding with that portion of the HIV virion which is necessarily interactive with T4 surface proteins during HIV infection of host cells and characterized by the capacity to neutralize infectivity of HIV in vitro and by specific immunoreactivity with an antibody immunospecific for human lymphocyte T4 to form an immunological reaction mixture including said protein and said polypeptide and isolating said protein from said reaction mixture.

4. A method for isolating HIV proteins from a fluid sample, said method comprising contacting said sample with a monoclonal anti-monoclonal-anti-human lymphocyte T4 antibody to form an immunological reaction mixture including said protein and said antibody and isolating said protein from said reaction mixture.

* * * * *

UNITED STATES PATENT AND TRADEMARK OFFICE
CERTIFICATE OF CORRECTION

PATENT NO. : 5,180,660
DATED : January 19, 1993
INVENTOR(S) : Tsuneya Ohno

It is certified that error appears in the above-indentified patent and that said Letters Patent is hereby corrected as shown below:

On the title page of the patent insert the following:

Item [56] --OTHER PUBLICATIONS

Abrams et al., Methods in Enzymology, 121, 107-119 (1986)
Beretta et al., Eur. J. Immunol., 17, 1793-1798 (1987)
Barnes, Science, Research News, 233, 1149-1153 (1986)
Borrebaeck, TIBTECH, 147-153 (1986)
Chanh et al., EMBO Journal, 5(11), 3065-3071 (1986)
Chanh et al., Eur. J. Immunol., 16, 1465-1468 (1986)
Chanh et al., P.N.A.S. (USA), 84, 3891-3895 (1987)
Chanh et al., Federation Proceedings, 46(4), p. 1352, No. 6041(1987)(Abstract)
Crowl et al., Cell, 41, 979-986 (1985)
Dalgleish, AIDS, 2, (suppl. 1), S129-S131 (1988)
Dalgleish et al., Nature, 312, 763-767 (1984)
Dalgleish et al., The Lancet, 1047-1050 (1987)
Deen et al., Nature, 331, 82-83 (1988)
Finberg et al., CRC Critical Reviews in Immunology, 7, 269-284 (1987)
Fischenger et al., Cancer Res., 45 (suppl.) 4694S-4690S (Sep. 1985)
Fisher et al., Nature, 331, 76-77 (1988)
Gallo, Scientific American, 256, 47-56 (1987)
Gallo, Scientific American, 255, 88-98 (1986)
Goding, J. Immunol. Meth., 39, 285-308 (1980)
Guroff et al., Nature, 316, 72-74 (1985)
Ho et al., J. Virol., 61, 2024-2028 (Jun. 1987)
Homsy et al., Immunol. Today, 8, 190-193 (1987)
Hoxie et al., Science, 234, 1123-1127 (1986)
Hussey et al., Nature, 331, 78-81 (1988)
Jerne et al., EMBO J., 243-247 (1982)
Jerne, Scientific American, 52-60 (1973)
Joyce, New Scientist, p. 26 (1987)
Kennedy et al., AIDS, 2, (suppl. 1) S119-S127 (1988)
Kennedy et al., Scientific American, 225, 48-56 (1986)

UNITED STATES PATENT AND TRADEMARK OFFICE
CERTIFICATE OF CORRECTION

PATENT NO. : 5,180,660

DATED : January 19, 1993

INVENTOR(S) : Tsuneya Ohno

It is certified that error appears in the above-indentified patent and that said Letters Patent is hereby corrected as shown below:

Kennedy et al., Science, 231, 1556-1559 (1986)
Kennedy, Science, 232, 220-223 (1986)
Klatzmann et al., Science, 225, 59-62 (1984)
Klatzmann et al., Science, 312, 767-768 (1984)
Klausner, Bio/Technology, 4, 1042-1043 (1986)
Klausner, Bio/Technology, 5, 867-868 (1987)
Koprowski et al., "Anti-Idiotype Vaccines Against Viral Infections," Concepts in Viral Pathogenesis II, Notkins et al., eds., Springer-Verlag, NY (1986) 401-411
Koprowski, Cancer Res. (suppl.), 45, 4689S-4690S (1985)
Kozbor et al., Methods in Enzymology, 121, 120-140 (1986)
Lane et al., Ann. Rev. Immunol., 3, 477-500 (1985)
Laurence, AIDS, 2, (suppl. 1), S91-94 (1988)
Laurence, Scientific American, 84-93 (1985)
Levy et al., Science, 225, 840-842 (1984)
Ludwig et al., Medical Hypotheses, 23(3), 303-307 (1987)
Maddon et al., Cell, 47, 333-348 (1986)
Marrack et al., Scientific American, 254, 36-45 (1986)
Marx, Science, 162-165 (1985)
Marx, Science, 229, 455-456 (1985)
Masuho et al., Biochem. & Biophys. Res. Comm., 135(2), 495-500 (1986)
Matsushita et al., Abstract No. W.3.2., p. 106, III International Conference on Acquired Immunodeficiency Syndrome, Jun. 1-5, 1987
Matthews et al., P.N.A.S. (USA), 83, 9709-9713 (1986)
McDougal et al., J. Immunology, 135, 3151-3162 (1985)
McDougal et al., J. Immunology, 137, 2937-2944 (1986)
McDougal et al., Science, 231, 382-385 (1986)
Methods in Enzymology, 121, "Immunochemical Techniques," Part I, Langone et al., eds. Academic Press, Inc. (N.Y. 1986) Index Only
Mitsuya et al., Nature, 325, 773-778 (1987)

UNITED STATES PATENT AND TRADEMARK OFFICE
CERTIFICATE OF CORRECTION

PATENT NO. : 5,180,660
DATED : January 19, 1993
INVENTOR(S) : Tsuneya Ohno

Page 3 of 5

It is certified that error appears in the above-indentified patent and that said Letters Patent is hereby corrected as shown below:

"Mobilizing Against Aids", Institute of Medicine, National
   Academy of Sciences, Harvard University Press,
   Cambridge, MA 1986 (Not Enclosed)
New Scientist, p. 7 (Dec. 18, 1986)
Newmark, Nature, 324, 304-305 (1986)
Norman, Science, 230, 1355-1358 (1985)
Oi et al., Sel. Methods Cell., 351-372 (1979)
Pert et al., P.N.A.S. (USA), 83, 9254-9258 (1986)
Poiesz et al., P.N.A.S. (USA), 77, 7415-7419 (1980)
Principles and Practice of Infectious Diseases (Second Edition), Mandell
   et al., eds., John Wiley & Sons, N.Y. 1694-1698 (Not Enclosed)
Putney et al., Science, 234, 1392-1395 (1986)
Robey, Science, 228, 593-595 (1985)
Robey, P.N.A.S. (USA), 83, 7023-7027 (1986)
Sattentau et al., Science, 234, 1120-1123 (1986)
Scientific American, pp. 86-88 (Feb. 1987)
Staerz et al., P.N.A.S. (USA), 83, 1453-1457 (1986)
Stewart et al., J. Immunol., 136, 3773-3778 (1986)
Suresh et al., Methods in Enzymology, 121, 210-228 (1986)
Traunecker et al., Nature, 331, 84-86 (1988)
Van Brunt, Bio/Technology, 5, 421-422 (1987)
Weiss, Nature, 331, p. 115 (1988)
Zhou et al., J. Immunol., 139(9), 2950-2956 (1987)
Zoler, Bio/Technology, No. 1984, 923-924
Kennedy, New Scientist, Abstract No. TH.9.5, p. 26 (June 11, 1987)
Allan et al., Science, 228, 1091-1094 (1985)
Chanh et al., "Monoclonal Anti-idiotypic antibody mimics the CO4 receptor
   and bends to human immunodeficiency virus" P.N.A.S. (USA) 84,
   3891-3895 (1987)
Zhou et al., Federation Proceedings, 46(4), p. 1352, No 6040 (1987)
McDougal et al., "Binding of HTLVIII/LAV to T4+ Cells by a Complex of the 110K
   Viral Protein and the T4 Molecule," Science, 231 282-385 (1986)

UNITED STATES PATENT AND TRADEMARK OFFICE
CERTIFICATE OF CORRECTION

PATENT NO. : 5,180,660
DATED : January 19, 1993
INVENTOR(S) : Tsuneya Ohno

Page 4 of 5

It is certified that error appears in the above-indentified patent and that said Letters Patent is hereby corrected as shown below:

Sattent, et al., "Epitopes of the CD4 Antigen and HIV Infection", Science, 234 (1986) 1120-1123

Baretta et al., "HIV env glycoprotein shares a cross-receiving epitope with a surface protein present on activated human monocytes and involved in antifen presentation", Eur. J. Immunol., 17, 1793-1798 (1987)

Putney et al., "HTLV-III/LAV-Neutralizing Antibodies to an E. Coli-Produced Fragment of the Virus Envelope", Science 234 (1986) 1392-1395

Hoxii et al., "Attrations in T4 (CD4) Protein and mRNA Synthesis in Cells Infected with HIV," Science, 234, 1123-1127 (1986)

McDougal et al., "Binding of the Human retrovirus HTLV-II/LAV/ARV/HIV to the CD4 (T4) Molecule: Conformation Dependence, Epitope Mapping, Antibody Inhibition and Potential for Idiotypic Minicry", J. Immunol., 137, 2937-2944 (1986)

Maddon, "The T4 Gene Encodes the AIDS Virus receptor and is Expressed in the Immune System and the Brain", Cell, 47, 333-348 (1986)

Pert, "Octapeptides deduced from the Neuropeptide receptor-inhibit human immunodeficiency virus receptor binding and T-Cell Infectivity", P.N.A.S. (USA), 83, 9254-9258 (1986)--

At Column 1, lines 44 and 45, replace "Klatzman" with --Klatzmann--.

At Column 2, line 14, after Science, delete "4" and insert --234--.

At Column 5, line 22, replace "graphiclly" with --graphically--.

At Column 5, line 49, replace "neutralizaitn" with --neutralization--.

At Column 6, line 19, replace "miligram" with --milligram--.

At Column 7, lines 36-37, replace "car-bonatebicarbonate" with --carbonate-biocarbonate--.

At Column 11, line 24, replace "IgG1" with --$IgG_1$--.

UNITED STATES PATENT AND TRADEMARK OFFICE
CERTIFICATE OF CORRECTION

PATENT NO. : 5,180,660
DATED : January 19, 1993
INVENTOR(S) : Tsuneya Ohno

It is certified that error appears in the above-identified patent and that said Letters Patent is hereby corrected as shown below:

At Column 11, line 54, replace "t" with --the--.

At Column 11, line 55, after "sulfuric" insert --acid--.

At Column 11, line 56, after "The" insert --results of the--.

At Column 11, line 57, after "FIG. 1" insert --and indicate--.

At Column 11, line 62, replace "preparation" with --preparations--.

At Column 11, line 63, delete "6x20 $10^3$", insert --6x$10^3$--.

At Column 12, line 4, replace "form" with --from--.

At Table 5, insert --Neutralization-- as a heading under Table 5.

At Table 6, replace "HIV-IIB" with --HIV-IIIB--.

At Column 15, line 34, replace "complementmediated" with --complement-mediated--.

At Column 16, lines 30-31, replace "an-timonoclonal" with --anti-monoclonal--.

Signed and Sealed this

Third Day of May, 1994

BRUCE LEHMAN

Attest:

Attesting Officer

Commissioner of Patents and Trademarks